United States Patent [19]

Varaprath et al.

[11] Patent Number: 5,152,984
[45] Date of Patent: Oct. 6, 1992

[54] HAIR FIXATIVES

[75] Inventors: Padmakumari J. Varaprath; Judith M. Vincent, both of Midland, Mich.

[73] Assignee: Dow Corning Corporation, Midland, Mich.

[21] Appl. No.: 616,290

[22] Filed: Nov. 20, 1990

[51] Int. Cl.⁵ .................. A61K 7/06; A61K 7/00
[52] U.S. Cl. ........................ 424/70; 424/47; 424/71; 424/DIG. 2; 132/202
[58] Field of Search .............. 424/47, 70, 71, 78, 424/DIG. 1, DIG. 2; 252/DIG. 13, 174.15

[56] References Cited

U.S. PATENT DOCUMENTS

| | | | |
|---|---|---|---|
| 2,643,375 | 6/1953 | Gant | 424/71 X |
| 2,676,182 | 4/1954 | Daudt et al. | 252/49.6 |
| 2,921,950 | 1/1960 | Jex et al. | 260/448.2 |
| 3,433,780 | 3/1969 | Cekoda et al. | 524/157 X |
| 3,493,424 | 2/1970 | Mohrlok et al. | 524/588 X |
| 4,424,297 | 1/1984 | Bey | 524/773 X |
| 4,501,619 | 2/1985 | Gee | 106/287.16 X |
| 4,620,878 | 11/1986 | Gee | 106/287.16 X |
| 4,902,499 | 2/1990 | Bolich, Jr. et al. | 424/70 |

FOREIGN PATENT DOCUMENTS

| | | | |
|---|---|---|---|
| 791168 | 7/1968 | Canada. | |
| 174097 | 3/1986 | European Pat. Off. | 424/71 |
| 889001 | 2/1962 | United Kingdom. | |

*Primary Examiner*—Thurman K. Page
*Assistant Examiner*—Sally Gardner
*Attorney, Agent, or Firm*—Jim L. DeCesare

[57] ABSTRACT

A new composition of matter which is an aminofunctional silicone resin. The aminofunctional resin is formed by the reaction of an aminofunctional silane and a silicone resin. A hair treating composition is also disclosed which is a mixture of a film forming material and a solvent for the film forming material. The film forming material is the aminofunctional resin formed by reacting an aminofunctional silane and a silicone resin. A hair treating method for imparting curl retention to hair employing the resin as the film forming material is further described.

12 Claims, No Drawings

HAIR FIXATIVES

BACKGROUND OF THE INVENTION

This invention relates to new hair fixative compositions and to improved methods of providing curl retention to hair in which there is employed as the film forming ingredient certain organosilicon resins which are aminofunctional resins formed by reacting an aminofunctional silane with a nonpolar silicone resin.

Fixatives are designed to provide a temporary setting effect or curl to the hair, and while the most common fixative is a hair spray which is designed to be applied to the hair after the hair has been blow dried, several specialty type fixatives can be applied either after the hair is towel dried or to dry hair, in order to provide more body and volume to the hair, and to aid in styling, modeling, and sculpting of the hair into unique new looks. This is followed by application of a hair spray in the form of an aerosol or pump spray to maintain the shape and style of the hair and provide gloss and sheen to the hair, in addition to a well groomed and natural appearance. Such specialty type fixatives are marketed under various names including styling gels, styling cremes, styling mousses, styling foams, styling sprays, styling spritz, styling mists, styling glazes, styling fixes; sculpting lotions, sculpting gels, sculpting glazes, sculpting sprays; glossing gels, glossing spritz; shaping gels; forming mousses; modeling spritz; finishing spritz; fixing gels; and setting lotions.

Whether the fixative is the more common hair spray or a specialty type fixative, it will typically include a film forming additive as the hair holding agent. The film forming additive should provide hair holding properties and curl retention, little flaking or powder on combing, rapid curing or drying on hair, nonstickiness, and be easily removable by shampooing. Film forming additives are delivered by a solvent which is usually an alcohol such as ethanol or a mixture of an alcohol and water. In the case of aerosol formulations such as hairsprays and mousses, a propellant such as isobutane, butane, propane or dimethyl ether is an added part of the delivery system.

Examples of currently used film forming agents are shellac, polyvinylpyrrolidone-ethyl methacrylate-methacrylic acid terpolymer, vinyl acetate-crotonic acid copolymer, vinyl acetate-crotonic acid-vinyl neodeconate terpolymer, poly(vinylpyrrolidone)-ethyl methacrylate methacrylic acid copolymer, vinyl methyl ether-maleic anhydride copolymer, octylacrylamide-acrylate-butylaminoethyl-methacrylate copolymer, and poly(vinylpyrrolidone-dimethylaminoethyl-methacrylate) copolymer and derivatives. These particular polymers are most suitable for alcohol based formulations such as hair sprays and pumps, and are sometimes used in water-based hair fixative products.

Such resins typically contain carboxyl groups which must be neutralized to some degree to provide compatibility with water to facilitate removal by shampooing and the increase the flexibility of the film. The neutralization of the carboxyl groups can lead to relatively high solution viscosities. Furthermore, the high molecular weight of the better holding resins produces solutions which are high in viscosity. When loading is attempted above a level of six to seven percent by weight of the formulation, the high viscosity prevents the solution from breaking up into droplets, and a stream rather than a spray is produced. Although higher solids solutions of these resins are deliverable from containers which have valves with a small orifice, these valves are more prone to clogging. Thus, loading of these resins above a certain solids level is not practical. In addition these organic resins have poor hold when subjected to high humidity for long periods of time. Thus, a need exists for a fixative resin which is water compatible without neutralization, provides high humidity resistance, is compatible with hydrocarbon propellants and is capable of being formulated into high solids products.

In accordance with the present invention, a new hair fixative formulation is provided which includes an organosilicon film forming material. Specifically, the organosilicon film forming material is a silicone resin, and more particularly an aminofunctional resin. Collodial suspensions of silicone resins are disclosed in U.S. Pat. No. 3,433,780, issued Mar. 18, 1969; U.S. Pat. No. 3,493,424, issued Feb. 3, 1970; and in U.S. Pat. No. 4,424,297, issued Jan. 3, 1984. However, these patents relate to the use of silicone resins for the treatment of fabrics to render them resistant to soiling and as fillers in latexes; the treatment of fabric or carpeting in order to impart antislip, dulling, and dry-soiling resistance to the materials; and as release agents. Thus, there is no suggestion in these patents that a silicone resin would have utility as a film forming ingredient in a hair fixative formulation.

While U.S. Pat. No. 4,902,499, issued Feb. 20, 1990, relates to the use of certain silicone resins in hair care compositions, the '499 patent does not teach the particular silicone resins of the present invention which are aminofunctional resins. The '499 patent is also specifically directed to compositions which provide improved style retention and hair conditioning properties. To that end, conditioning moieties such as dialkylsiloxane are prominent. It is known that conditioning can adversely affect holding properties in fixative formulations. Therefore, the dialkylsiloxane moieties are eliminated or reduced in the present invention. Thus, this invention employs aminofunctional resins for set retention with improved hair-holding properties.

Silicones have two inherent properties particularly advantageous in hair holding applications. Certain silicone materials form films which are hydrophobic and produce solutions of low viscosity. The aminofunctional resins of the present invention have been found to provide higher humidity resistance than organic film forming materials at lower add-on levels. In contrast to the organic resins, their solution viscosity is low, even at high loading. This characteristic provides resins which can be formulated at higher solids levels than permitted by current formulations.

An unexpected benefit derived from low solution viscosity is the improved spray patterns that the materials of the present invention exhibit when delivered through an orifice of industry standard size. Even at solids levels as high as 15 percent by weight, the resin solutions yield well-dispersed spray patterns. Unlike the organic film formers, the silicone resins do not require neutralization to provide water compatibility. Additionally, the materials of the present invention permit variations in hold from harsh to soft hold through structure modifications. This is in contrast again to the organic polymers which are harsh holding when minimally neutralized and can only provide soft hold through neutralization, which in turn, comprises high humidity resistance. Furthermore, the silicone resins offer additional advantages including compatibility with ethanol and hydrocarbon propellants, good sheen, low buildup, lack of tackiness, nonirritability, and reduced flaking.

SUMMARY OF THE INVENTION

This invention relates to a new composition of matter. The new composition of matter is an aminofunctional silicone resin. The aminofunctional resin is formed by the reaction of an aminofunctional silane and a silicone resin.

The invention is also directed to a hair treating composition which is a mixture of a film forming material and a solvent for the film forming material. The film forming material is the aminofunctional silicone resin formed by reacting an aminofunctional silane and a silicone resin.

The invention is further directed to a hair treating method for imparting curl retention to hair in which a film forming material is applied to hair. The improvement in accordance with the present invention resides in utilizing as the film forming material an aminofunctional resin which is the reaction product of an aminofunctional silane and a silicone resin.

These and other features, objects, and advantages, of the present invention will become more apparent when considered in light of the following detailed description thereof.

DETAILED DESCRIPTION OF THE INVENTION

As noted above, the present invention relates to hair fixatives which utilize as the film forming ingredient a silicone resin which is aminofunctional. Such silicone resins have been found to exhibit improved curl retention in comparison to conventional organic systems, and provide the advantages of ethanol solubility, water compatibility, nonirritability, excellent aesthetics on hair, shampoo removability, good sheen, improved hold, low buildup, nontacky, and reduced flaking. The silicone resins of the present invention also offer the added benefit that a plasticizer is not required, although plasticizers may be included in the fixative composition if desired. Organic fixative systems include GANTREZ ® resins which are polymers consisting of the partial ethyl ether of the polycarboxylic resin formed from vinyl methyl ester and maleic anhydride. GANTREZ ® ES 225 is a product of the GAF Corporation, Wayne N.J., and a trademark of the GAF Corporation. This resin has been the film forming ingredient in such products as WHITE RAIN ® and FINAL NET ®. Such resins are typically employed as an ethanol based pump spray.

The aminofunctional silicone resins also have application in aqueous-alcohol based hair fixative systems. Aqueous ethanol for example is employed in some commercial spray-on pump and aerosol type products and mousses. The function of the alcohol in such systems is to promote faster drying of the formulation relative to the water based type system. In addition, the aminofunctional resins of the present invention may be used in anhydrous alcohol systems whether the system is designed for aerosol delivery or delivery by means of a pump spray device.

In the hair treating method in accordance with the present invention, the film forming ingredient is an organosilicon compound which is an aminofunctional silicone resin formed by reacting an aminofunctional silane with a silicone resin. The silicone resin has a formula selected from the group consisting of

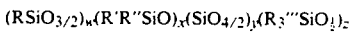

and hydroxy, alkoxy, aryloxy, and alkenoxy, derivatives thereof, wherein R, R', R'', and R''', are selected from the group consisting of alkyl, alkenyl, aryl, and alkylaryl, radicals having from one to twenty carbon atoms; and w, x, y, and z, are each integers having a value of from zero to about one thousand, with the proviso that the sum of integers w and y must be at least one. Silicone resin materials conforming to any one of the above specified generic formulas are commercially available from the Dow Corning Corporation, Midland, Mich.

The aminofunctional silicone resins are applied to the hair as a mixture including a solvent. The organosilicon compound is present in the mixture at a level from about 0.1 to about fifty percent by weight based on the weight of the mixture. Preferably, the organosilicon compound is present in the mixture at a level from about three to about thirty percent by weight based on the weight of the mixture. The solvent may be a hydrocarbon, an alcohol, or a blend of alcohol and water. Other solvents which may be employed include supercritical fluids such as supercritical carbon dioxide and nitrogen; volatile silicones including linear and cyclic siloxanes; hydrocarbons; and in some instances aqueous emulsion systems may also be appropriate. Where the solvent is a hydrocarbon, it is preferred to employ materials such as dimethylether, liquefied petroleum gas, propane, and isobutane. In the event the solvent is an alcohol, some appropriate materials are methanol, ethanol, and isopropanol. The aminofunctional resins can be applied to the hair as a mixture including a solvent and at least one additional ingredient such as propellants, conditioners, surfactants, plasticizers, thickeners, preservatives, and fragrances.

The aminofunctional resins of the present invention were dissolved in ethanol and tested for curl retention. These formulations were compared to a commercial aerosol product containing GANTREZ ® as the film forming resin ingredient. The resin materials of the present invention provided curl retentions equivalent to the curl retention obtained with the organic commercial product. In experiments involving multiple hair tresses, the materials of the present invention provided more consistent results than the corresponding commercial product. The results of these tests and their procedures are set forth below.

The following examples are set forth in order to illustrate in more detail the concepts embodied by the present invention.

EXAMPLE I

Into a three neck round bottom flask equipped with a stirrer and thermometer was placed 39.8 grams toluene and 14.4 grams isopropanol. To this was added 33.6 grams phenyltrichlorosilane and 12.2 grams propyltrichlorosilane. Water was added to hydrolyze the chlorosilanes in an amount to produce an aqueous phase containing 13–16 weight percent hydrochloric acid. This mixture was refluxed for four hours insuring continuous hydrolysis. The hydrolyzate was separated from the aqueous phase, the solvent was removed under vacuum, and the solid product was flaked. The product corresponded to a nonpolar silsesquioxane of the formula $RSiO_{3/2}$.

EXAMPLE II

Into a three neck round bottom flask equipped with a stirrer and thermometer was placed 42.3 grams toluene and 7.6 grams isopropanol. To this was added 22.7 grams phenyltrichlorosilane, 18.2 grams of methyltrichlorosilane, 2.5 grams of phenylmethyldichlorosilane, and 6.8 grams of diphenyldichlorosilane. Water was added to hydrolyze the chlorosilanes in an amount to produce an aqueous phase containing 13-16 weight percent hydrochloric acid. This mixture was refluxed for four hours insuring continuous hydrolysis. The hydrolyzate was separated from the aqueous phase, the solvent was removed under vacuum and the solid product was flaked. The product corresponded to a silicone resin of the formula

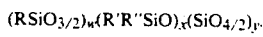

Resins preferred in accordance with the present invention are those produced from the chlorosilanes or alkoxysilanes shown in Table I.

TABLE I

| | Mole Percent Ratios of Preferred Silane | | | | | | | |
|---|---|---|---|---|---|---|---|---|
| | Mole Percent | | | | | | | Weight Percent |
| Resin | Me | Me2 | Ph | Ph2 | PhMe | Pr | Me3 | Metallic Salt |
| 1 | — | — | 70 | — | — | 30 | — | — |
| 2 | 45 | — | 40 | 10 | 5 | — | — | — |
| 3 | 32 | 29.3 | 38.7 | — | — | — | — | — |
| 4 | 63-66 | 0.8 | 31-33 | — | — | — | 0.7 | — |
| 5 | 60 | — | 30 | 10 | — | — | — | — |
| 6 | 25 | 19 | 37 | 19 | — | — | — | — |
| 7 | 25 | 19 | 37 | 19 | — | — | — | 1.2* |

*Zinc Octoate added at 1.2 percent based on weight of resin

EXAMPLE III

The process used to make the silicone resin of this example is shown in U.S. Pat. No. 2,676,182. A general description follows. Twenty-two grams sodium silicate was added to a refrigerated flask equipped with a stirrer and thermometer. To this was added 19.3 grams hydrochloric acid. After exotherm, 6.9 grams of isopropanol and 22.0 grams of trimethylchlorosilane was added, heat applied and refluxing continued for a period of time. 1.8 grams polydimethylsiloxane was added and heating was continued. The product was separated from the aqueous phase and this material was a silicone resin of the formula

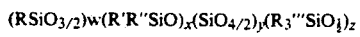

at a weight percent level of 46 and $Me_3SiOSiMe_3$ at a weight percent level of 54.

The aminofunctional silane which is reacted with the silicone resin to form the aminofunctional resin of the present invention can be a silane such as
3-aminopropyltrimethoxysilane,
N-(2-aminoethyl)-3-aminopropyltrimethoxysilane,
N-(aminoethylaminomethyl) phenyltrimethoxysilane,
N-(2-aminoethyl)-3-aminopropyl tris(2-ethylhexoxy)silane, and
bis(2-hydroxyethyl)-3-aminopropyltrimethoxysilane.

Quaternary ammonium functional silanes can also be used such as
3-(trimethoxysilyl) propyloctadecyldimethyl ammonium chloride, 2-methacryloxyethyldimethyl (3-trimethoxysilylpropyl) ammonium chloride, and
2-hydroxyethyldimethyl (3-trimethoxysilypropyl) ammonium chloride.

The most preferred aminofunctional silane is N-(2-aminoethyl)-3-aminopropyltrimethoxysilane. This aminoalkylfunctional silane is a low viscosity liquid having a viscosity of about six centistokes measured at twenty-five degree Centigrade, and is a reactive fluid containing an alkylamine organic group and a trimethoxysilyl inorganic group. These aminofunctional silanes and methods for their preparation are well known in the art. Such silanes are commercially available from the Dow Corning Corporation, Midland, Mich. Structural formulas for some aminofunctional silanes which may be employed in accordance with the present invention are set forth below.

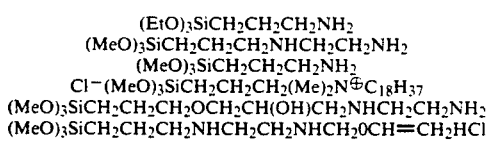

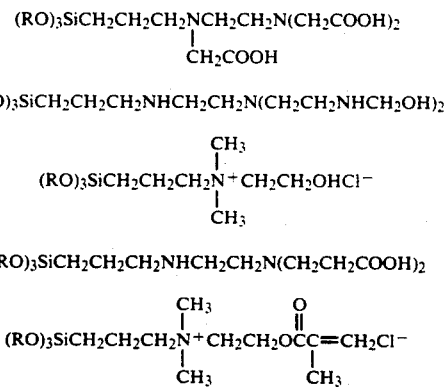

The aminofunctional resins of the present invention are formed in accordance with the following reaction:

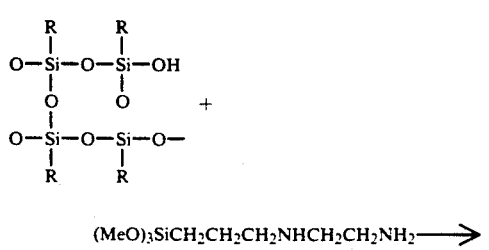

-continued

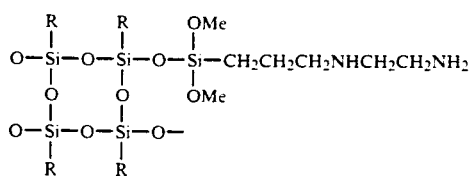

An example illustrating this reaction is set forth below.

EXAMPLE IV

Into a five hundred milliliter three necked flask equipped with a nitrogen inlet, thermometer, distilling head, condenser, and a magnetic stirring bar was added thirty grams of silicone resin and one hundred grams of toluene. The mixture was stirred until the resin dissolved. The solution was heated to between seventy and eighty degrees Centigrade and 6.53 grams of N-(2-aminoethyl)-3-aminopropyltrimethoxysilane was added. Heating at this temperature range was continued for one hour under a slow nitrogen flow. Methanol and water were removed overhead. The solution was cooled and toluene was removed. The aminofunctional resin product was removed.

EXAMPLE V

Example IV was repeated except that 13.3 grams of N-(2-aminoethyl)-3-aminopropyltrimethoxysilane was added.

EXAMPLE VI

Example IV was repeated except that 26.1 grams of N-(2-aminoethyl)-3-aminopropyltrimethoxysilane was added.

EXAMPLE VII

Example IV was repeated except that forty grams of N-(2-aminoethyl)-3-aminopropyltrimethoxysilane was added.

EXAMPLE VIII

The aminofunctional resins of Examples IV-VII were formulated into hair fixative compositions by mixing with ethanol to provide various fixative formulations containing three, five, and ten weight percent resin.

EXAMPLE IX

Hair fixative formulations were evaluated by employing six inch hair tresses of approximately two grams of untreated human hair. Each tress was made by gluing the top part of the hair to a 2"×2" plastic tab. After drying on the tab, the hair was trimmed to six inches. Each tress was then cleaned with an anionic shampoo of the following formulation:

| | |
|---|---|
| Distilled Water | 61.45% |
| Methylchlorisothiazolinone and methylisothiazolinone | 0.05% |
| Ammonium Lauryl Sulfate | 35.00% |
| Lauramide DEA | 3.00% |
| Sulfuric Acid | q.s. |
| Ammonium Chloride | 0.50% |

The tress was first rinsed for 15 minutes under 40 degree Centigrade tap water and 0.5 cc of the above shampoo was applied. Shampooing for 30 seconds was followed by a 30 second rinse. The tresses were then set on plastic rollers approximately ½ inch in diameter and allowed to dry overnight. Hair fixative formulations were applied to the hair either by dripping on 0.5 g or by spraying on 0.3 g. If the drip application was used, the hair was combed three times and reset on a roller. If the resin solution was delivered from a pump, the hair was not reset. The solution was allowed to cure on the hair for a period of one to two hours. The dried tresses were hung in a constant humidity chamber at 90 percent relative humidity and initial readings were taken as well as additional readings at predetermined intervals. If the tress was reset, the roller was removed prior to exposure. Curl retention was calculated as the extended length minus the length at the end of the predetermined interval divided by the extended length minus the initial length. The results shown in Table II represent curl retention after 24 hours of exposure.

GANTREZ ® ES225 resin which is a polymer of the partial ester of the carboxylic resin formed from vinyl methyl ester and maleic anhydride was used as the control comparison. This organic resin is frequently used in ethanol based hair holding formulations such as aerosols and pumps.

TABLE II

| Resin (Example) | Weight Percent of Resin | Test Method | Curl Retention (Percent) |
|---|---|---|---|
| IV | 5 | Drip | 80 |
| V | 3 | Drip | 90 |
| V | 5 | Drip | 92 |
| V | 10 | Drip | 97 |
| VI | 3 | Drip | 91 |
| VI | 5 | Drip | 99 |
| VI | 10 | Drip | 98 |
| GANTREZ ® | 3 | Drip | 91 |
| GANTREZ ® | 5 | Drip | 91 |
| GANTREZ ® | 10 | Drip | 94 |
| V | 5 | Pump | 75 |
| VI | 5 | Pump | 88 |
| VII | 5 | Pump | 93 |
| VII | 10 | Pump | 94 |
| GANTREZ ® | 5 | Pump | 80 |

Table II indicates that the aminofunctional resin formulations prepared in accordance with the present invention provided curl retention at least equivalent to the curl retention of the organic material GANTREZ ®. The aminofunctional resins are soluble in ethanol and provide good hair holding properties. These resins have lower solution viscosities and hence allow an easier delivery in spray pump applications. Acceptable shampoo removability is also provided by the resin materials of the present invention.

The compositions of this invention may contain an emulsifying agent selected from the group consisting of anionic, amphoteric nonionic, cationic, and zwitterionic surfactants. Suitable anionic detergents include sulfonated and sulfated alkyl, aralkyl and alkaryl anionic detergents; alkyl succinates; alkyl sulfosuccinates and N-alkyl sarcosinates. Surfactants generally classified as amphoteric or ampholytic detergents include, among others, cocoamphocarboxyglycinate, cocoamphocarboxypropionate, cocobetaine, N-cocamidopropyldimethylglycine, and N-lauryl-N-carboxymethyl-N-(2-hydroxyethyl)ethylenediamine. Other suitable amphoteric detergents include the quaternary cycloimidates, betaines, and sultaines disclosed in U.S. Pat. No. 3,964,500. The compositions of this invention may contain a nonionic surfactant. The nonionic surfactants of the present invention are selected from the group consisting of fatty acid alkanolamide and amine oxide surfactants. Appropriate cationic surfactants in accordance with the present invention include quaternary ammonium salts of primary, secondary, and tertiary fatty amines. Zwitterionic surfactants which may be employed are quaternary ammonium, phosphonium, and sulfonium compounds containing aliphatic substituents one of which is carboxy, phosphate, phosphonate, sulfate, or sulfonate functional.

Other adjuvants may be added to the compositions of this invention such as plasticizers, thickeners, perfumes, colorants, electrolytes, pH control ingredients, antimicrobials, antioxidants, ultraviolet light absorbers and medicaments. When the fixative is in the form of a gel or lotion, it is sometimes preferred to employ a thickener in the compositions to facilitate the hand application of the composition to the hair. Thickeners are preferably used in sufficient quantities to provide a convenient viscosity. For example, viscosities within the range of 400 to 6000 cps are preferred for lotions. Higher viscosities are preferred for gels whereas lower viscosities are preferred for sprays.

Suitable thickeners, include, among others, sodium alginate, gum arabic, polyoxyethylene, guar gum, hydroxypropyl guar gum, cellulose derivatives such as methylcellulose, methylhydroxypropylcellulose, hydroxypropylcellulose, polypropylhydroxyethlcellulose, starch and starch derivatives such as hydroxyethylamylose, and starch amylose, locust bean gum, electrolytes such as NaCl, saccharides such as fructose and glucose, and derivatives of saccharides such as PEG-120 methyl glucose dioleate. Preferred thickeners include the cellulose derivatives and saccharide derivatives. The glucose derivative, PEG-120 methyl glucose dioleate, is especially preferred in the present invention. Electrolytes including sodium chloride and ammonium chloride provide thickening particularly in aqueous systems and may also be employed in accordance with the present invention.

Representative plasticizers that may be employed include polyproplylene glycol, glycerine, and polysiloxanes. Siloxane polymers such as polydimethylsiloxane, cyclic polydimethylsiloxane, phenylpolydimethylsiloxane, and polydimethylsiloxane with methylene and/or propylene oxide side chains, are particularly preferred in accordance with the present invention.

The perfumes which can be used in the compositions must be cosmetically acceptable perfumes. Colorants are used to confer a color to the composition and may generally be used. Although not required, it is preferred to employ an acid or base to adjust the pH within the range of 5 to 9 or more preferably within the range of 6 to 8 in the compositions of this invention. Any water soluble acid such as a carboxylic acid or a mineral acid is suitable. For example, suitable acids include mineral acids such as hydrochloric, sulfuric, and phosphoric, monocarboxylic acids such as acetic acid, lactic acid, or propionic acid; and polycarboxylic acids such as succinic acid, adipic acid and citric acid. Where a base is required, organic amines such as 2-amino-2-methyl-1-propanol are appropriate.

If for special purposes conditioners are desired, they may be added. For example, any of the well-known organic cationic hair conditioning components may be added. Some cationic conditioning components that may be used in the present invention to provide hair grooming include quaternary nitrogen derivatives of cellulose ethers, homopolymers of dimethyldiallylammonium chloride, copolymers of acrylamide and dimethyldiallylammonium chloride, homopolymers or copolymers derived from acrylic acid or methacrylic acid containing cationic nitrogen functional groups attached to the polymer via ester or amide linkages, polycondensation products of N,N'-bis-(2,3-epoxypropyl)-piperazine or of piperazine-bis-acrylamide and piperazine, poly-(dimethylbutenylammonium chloride)-α,ω-bis-(triethanol-ammonium) chloride, and copolymers of vinylpyrrolidone and acrylic acid esters with quaternary nitrogen functionality. The above cationic organic polymers and others are described in more detail in U.S. Pat. No. 4,240,450 which is hereby incorporated by reference to further describe the cationic organic polymers. Other categories of organic conditioners may also be employed such as proteins, monomeric organic quaternaries and betaines. Silicone conditioning agents may also be employed such as cyclomethicone, dimethicone, phenyldimethicone, dimethicone copolyol, amodimethicone, and trimethylsilylamodimethicone.

A preservative may be required and representative preservatives which may be employed include about 0.1–0.2 weight percent of compounds such as formaldehyde, dimethyloldimethylhydantoin, 5-bromo-5-nitro-1,3-dioxane, methyl- and propyl para-hydroxybenzoates, and mixtures of such benzoates with sodium dehydroacetate, sorbic acid, and imidazolidinyl urea.

The compositions of the present invention may also be formulated to include dyes, colorants, reducing agents, neutralizing agents, and preservatives, necessary for their application as permanent wave systems or hair dyes, for example. The active formulation can be applied in several different forms including lotions, gels, mousses, aerosols, and pump sprays, for example, and as conditioners and shampoos. The active ingredient includes a carrier, and suitable carrier fluids for hair care formulations are water as well as, for example, such fluids as alcohols namely ethanol or isopropanol, hydrocarbons and halogenated hydrocarbons such as mineral spirits and trichloroethane, supercritical fluids such as supercritical carbon dioxide and nitrogen, cyclic siloxanes, and aerosol propellants. In those instances where it is desired to incorporate the active in the form of either an emulsion or microemulsion, such emulsions may be prepared in accordance with either U.S. Pat. No. 4,501,619, issued Feb. 26, 1985, which is directed to emulsions, or U.S. Pat. No. 4,620,878, issued Nov. 4, 1986, relating to microemulsions, each of which is incorporated herein by reference.

When the composition is intended for aerosol application, propellant gases can be included such as carbon dioxide, nitrogen, nitrous oxide, volatile hydrocarbons such as butane, isobutane, or propane and chlorinated or fluorinated hydrocarbons such as dichlorodifluoromethane and dichlorotetrafluoroethane or dimethylether. Where the solvent system is alcohol free, mechanical and chemical drying agents may also be employed in spray and aeroxol formulations.

Additional aminofunctional silanes which may be employed in accordance with the present invention include
4-aminobutyldimethylmethoxysilane,
4-aminobutyltriethoxysilane,
N-(2-aminoethyl)-3-aminopropylmethyldimethoxysilane, 6-(aminohexylaminopropyl)trimethoxysilane,
trimethylsilylmethylamine, aminophenyltrimethoxysilane,
3-(1-aminopropoxy)-3,3-dimethyl-1-propenyltrimethoxysilane,
3-aminopropyldiethylmethylsilane,
3-aminopropyltris(methoxyethoxyethoxy)silane,
3-aminopropyldimethylethoxysilane,
3-aminopropylmethyldiethoxysilane,
3-aminopropyltriethoxysilane, and
3-aminopropyltris(trimethylsiloxy)silane.

It will be apparent from the foregoing that many other variations and modifications may be made in the compounds, compositions, and methods, described herein, without departing substantially from the essential features and concepts of the present invention. Accordingly, it should be clearly understood that the forms of the invention described herein are exemplary only and are not intended as limitations on the scope of the present invention as defined in the appended claims.

That which is claimed is:

1. An aminofunctional silicone resin comprising the reaction product of an aminofunctional silane and a silicone resin having a formula selected from the group consisting of $$RSiO_{3/2} \qquad (I)$$

$$(RSiO_{3/2})_w(R'R''SiO)_x(SiO_{4/2})_y \qquad (II)$$

$$(RSiO_{3/2})_w(R'R''SiO)_x(SiO_{4/2})_y(R_3'''SiO)_z \qquad (III)$$

wherein R, R', R'', and R''' are selected from the group consisting of alkyl, alkenyl, aryl, and alkylaryl radicals having from one to twenty carbon atoms; and w, x, y, and z are integers having a value of from zero to about one thousand with the proviso that the sum of w and y is at least one.

2. The method of claim 1 in which the silane is selected from the group consisting of 3-aminopropyltrimethoxysilane, N-(2-aminoethyl)-3-aminopropyltrimethoxysilane, N-(aminoethylaminomethyl) phenyltrimethoxysilane, N-(2-aminoethyl)-3-aminopropyl tris(2-ethylhexoxy)silane, bis(2-hydroxyethyl)-3-aminopropyltrimethoxysilane, and 3-(trimethoxysilyl) propyloctadecyldimethyl ammonium chloride.

3. The method of claim 1 in which the silane is N-(2-aminoethyl)-3-aminopropyltrimethoxysilane.

4. The method of claim 1 wherein the silicone resin has the formula $RSiO_{3/2}$ wherein R is selected from the group consisting of alkyl, alkenyl, aryl, and alkylaryl radicals having from one to twenty carbon atoms.

5. The method of claim 1 wherein the silicone resin has the formula $$(RSiO_{3/2})_w(R'R''SiO)_x(SiO_{4/2})_y.$$

6. The method of claim 1 wherein the silicone resin has the formula $$(RSiO_{3/2})_w(R'R''SiO)_x(SiO_{4/2})_y(R_3'''SiO_{1/2})_z.$$

7. The method of claim 1 in which the resin is applied to the hair as a mixture including a solvent, and in which the resin is present in the mixture at a level from about 0.1 to about fifty percent by weight based on the weight of the mixture.

8. The method of claim 1 in which the resin is applied to the hair as a mixture including a solvent, and in which the resin is present in the mixture at a level from about three to about thirty percent by weight based on the weight of the mixture.

9. The method of claim 8 in which the solvent is selected from the group consisting of volatile silicones, hydrocarbons, alcohols, supercritical fluids, and blends of alcohol and water.

10. The method of claim 9 in which the solvent is a hydrocarbon selected from the group consisting of dimethylether, liquefied petroleum gas, propane, and isobutane.

11. The method of claim 9 in which the solvent is an alcohol selected from the group consisting of methanol, ethanol, and isopropanol.

12. The method of claim 1 in which the resin is applied to the hair as a mixture including at least one additional ingredient selected from the group consisting of propellants, conditioners, surfactants, plasticizers, thickeners, preservatives, and fragrances.

* * * * *

UNITED STATES PATENT AND TRADEMARK OFFICE
CERTIFICATE OF CORRECTION

PATENT NO. : 5,152,984
DATED : Oct. 6, 1992
INVENTOR(S) : Padmakumari J. Varaprath and Judith M. Vincent It is certified that error appears in the above-identified patent and that said Letters Patent is hereby corrected as shown below: In column II, lines 22-38, Claim 1 should read as follows:

In a hair treating method for imparting curl retention to hair in which a film forming material is applied to hair, the improvement comprising utilizing as the film forming material an aminofunctional silicone resin which is the reaction product of an aminoalkoxysilane and a silicone resin, the silicone resin being a hydroxy derivative having a formula selected from the group consisting of $$RSiO_{3/2} \qquad (I)$$

$$(RSiO_{3/2})_w (R'R''SiO)_x (SiO_{4/2})_y \qquad (II)$$

$$(RSiO_{3/2})_w (R'R''SiO)_x (SiO_{4/2})_y (R_3'''SiO_{1/2})_z \qquad (III)$$

wherein R, R', R'', and R''' are selected from the group consisting of alkyl, alkenyl, aryl, and alkylaryl radicals having from one to twenty carbon atoms; x, y, and z are integers having a value of from zero to about one thousand and w is an integer having a value of one to about one thousand.

Signed and Sealed this

Twenty-sixth Day of April, 1994

*Attest:*

BRUCE LEHMAN

*Attesting Officer*     Commissioner of Patents and Trademarks